(12) United States Patent
Wu et al.

(10) Patent No.: US 8,685,698 B2
(45) Date of Patent: Apr. 1, 2014

(54) **YELLOW PIGMENTS GENERATION DEFICIENT *SPHINGOMONAS* STRAIN AND APPLICATION THEREOF IN GELLAN GUM PRODUCTION**

(75) Inventors: Xuechang Wu, Zhejiang (CN); Rongming Wu, Zhejiang (CN); Ou Li, Zhejiang (CN); Liang Zhu, Zhejiang (CN); Yamin Chen, Zhejiang (CN); Chaodong Qian, Zhejiang (CN); Mei Chen, Zhejiang (CN)

(73) Assignees: Zhejiang University, Zhejiang (CN); Zhejiang DSM Zhongken Biotechnology Co., Ltd., Zhejiang (CN)

( * ) Notice: Subject to any disclaimer, the term of this patent is extended or adjusted under 35 U.S.C. 154(b) by 51 days.

(21) Appl. No.: 13/142,412

(22) PCT Filed: Aug. 13, 2010

(86) PCT No.: PCT/CN2010/001228
§ 371 (c)(1),
(2), (4) Date: Jul. 21, 2011

(87) PCT Pub. No.: WO2011/035530
PCT Pub. Date: Mar. 31, 2011

(65) Prior Publication Data
US 2011/0281308 A1    Nov. 17, 2011

(30) Foreign Application Priority Data

Sep. 25, 2009  (CN) .......................... 2009 1 0153005

(51) Int. Cl.
*C12N 1/12* (2006.01)
*C12P 19/04* (2006.01)
(52) U.S. Cl.
USPC ...................................... 435/252.1; 435/101

(58) Field of Classification Search
None
See application file for complete search history.

(56) References Cited

U.S. PATENT DOCUMENTS

2003/0100078 A1    5/2003   Harding et al.

FOREIGN PATENT DOCUMENTS

| CN | 1553957 A | 10/2004 |
| CN | 1635132 A | 7/2005 |
| CN | 1970738 A | 5/2007 |
| CN | 101665778 A | 3/2010 |
| WO | WO03068004 A2 | 8/2003 |

OTHER PUBLICATIONS

Wang, Qin-dan et al. "Recent advance in gellan gum biosynthesis", *Food Sciences*, vol. 29, No. 10, pp. 689-693 (May 31, 2008).
Arsenio, M. et al., "Occurrence, production, and applications of gellan: current state and perspectives", *Applied Microbiology and Biotechnology*, vol. 79, No. 6, pp. 889-890 (May 28, 2008).

*Primary Examiner* — Robert Mondesi
*Assistant Examiner* — Iqbal H Chowdhury
(74) *Attorney, Agent, or Firm* — Drinker Biddle & Reath LLP

(57) ABSTRACT

A yellow pigments generation deficient *Sphingomonas* strain (*Sphingomonas* sp. ZD001) and application thereof in preparing gellan gum by microbial fermentation are provided. The strain is preserved in China Center for Type Culture Collection (CCTCC) with the address of Wuhan University, Wuhan, 430072, China, the preservation date of the strain is 10 Sep. 2009, and the preservation serial number is CCTCC No: M 209298. The main beneficial effect of the present invention is that the fermented liquor contains no yellow pigments but is milky white, colorless superior gellan gum can be obtained by only depositing polysaccharide with a small quantity of ethanol or isopropanol, so that the post purification and de-coloration techniques of gellan gum production can be simplified, the yield can be enhanced, and the production cost can be reduced.

7 Claims, No Drawings

YELLOW PIGMENTS GENERATION DEFICIENT *SPHINGOMONAS* STRAIN AND APPLICATION THEREOF IN GELLAN GUM PRODUCTION

TECHNICAL FIELD

The present invention is related to a strain, i.e., the *Sphingomonas* strain ZD001 (*Sphingomonas* sp. ZD001) which is characterized as being yellow pigments generation deficient and being capable of producing gellan gum having the normal quality, and to the application of this strain in the preparation of gellan gum via the fermentation of microorganism.

BACKGROUND

Gellan Gum is a microbial extracellular polysaccharide, produced by a *Sphingomonas* strain (*Sphingomonas paucimobilis*) via aerobic fermentation. This product was successfully developed by CP Kelco U.S., Inc. in 1978. It is another microbial extracellular polysaccharide after xanthan, which is non-toxic and safe, and shows good physicochemical properties. It was approved to be used in food products in Japan, as early as in 1988. The FDA of the USA government approved its use in foodstuff in 1992. In our country, it was approved to be used as a thickener or a stabilizer for food products in 1996. And there are more than ten of other countries, which have approved its use as an additive for food products. In recent years, gellan gum is increasingly and broadly used in food industry, medicine industry, chemical industry and other industrial fields, as a new emulsifier, a suspending agent, a thickener, a stabilizer, a gelling agent, a slow-released agent, a film-forming material and etc., due to its unique good properties. This shows a huge prospect of its applications being broadened.

Gellan gum is comprised of β-1,3-D-glucose, β-1,4-D-glucuronic acid and α-1,4-L-rhamnose in the mole ratio of 2:1:1, with the linking order of a β-1,3-D-glucose, a β-1,4-D-glucuronic acid, a β-1,3-D-glucose, and an α-1,4-L-rhamnose to form the tetrasaccharide unit. To the framework of long chains of sugars formed by the polymerization of tetrasaccharide units, there are acyl groups linked. The molecular weight of gellan gum normally is about $5 \times 10^5 - 1 \times 10^6$ daltons. Gellan gum mainly exists in two forms, i.e., the non-deacylated high acyl gellan gum (also called as native gellan gum), and the physically and/or chemically artificially-deacylated low acyl gellan gum. In the high acyl or native gellan gum, there are two kinds of acyl groups, namely, acetyl and glyceroyl. Usually, the acetyl groups are linked to the C 6 position of the first glucose residue while the glyceroyl groups are linked to the C 2 position of the same glucose residue. In general, for each tetrasaccharide unit, there is one glyceroyl group on average, and 0.5 acetyl groups on average. The low acyl gellan gum is a product substantially free of acyl groups, produced from high acyl gellan gum by a deacylation treatment. So, the molecules of gellan gum have various molecule weights showing large differences, depending upon whether the molecules are deacylated or not and how much degree the molecules are deacylated. At present, the low acyl gellan gum with a relatively low molecular weight has the most applications in food industry.

The gellan gum-producing bacterial strains currently used in production, *sphingomonas* strains, can co-produce the by-products through metabolism during fermentation process, i.e., the yellow pigments (mainly the pigments carotinoids), which not only competes the carbon source with gellan gum, but only makes the fermentation broth yellowing. During the preparation of gellan gum, particularly in the preparation of high acyl gellan gum, in order to remove the yellow pigments from the colloid, it needs to increase the amount of ethanol or isopropanol used in decoloration by extraction (in general, ethanol or isopropanol is used at the amount based on volume of 3 times of the volume of the fermentation broth), and the time for the operation. This reduces the efficiency of extraction and purification, leading to an increase on costs

SUMMARY OF INVENTION

One aim of the present invention is to provide a yellow-pigments generation-deficient strain, but being capable of producing gellan gum with normal quality, i.e., a *sphingomonas* strain, called as ZD001 (*Sphingomonas* sp. ZD001). The ZD001 strain has been deposited at China Center for Type Culture Collection (CCTCC), the address of the center: Wuhan University, Wuhan, China, Post Code 430072; and the preservation date of the strain: Sep. 10, 2009; the preservation serial number: CCTCC No: M209198. In the following text, the strain is called as ZD001 (CCTCC NO: M 209198) strain.

The technical solution adopted in the present invention is:

ZD001 (CCTCC NO: M 209198) strain is obtained by the separation and screening of the present inventors of this application. Through a sequencing of the 16S rDNA of this strain and a molecular comparison analysis, the strain has a homology of above 99% with the nucleotide sequence of 16S rDNA of the used *sphingomonas* strain (*Sphingomonas paucimobilis*). So, ZD001 (CCTCC NO: M 209198) strain is identified as a mutant strain of the reported gellan gum-producing *sphingomonas* strain, which still belongs to the same species as the reported gellan gum-producing *sphingomonas* strain.

The said ZD001 (CCTCC NO: M 209198) strain has a 16S rDNA with the following sequence:

```
AGAGTTTGATCCTGGCTCAGAACGAACGCTGGCGGCATGCCTAACACATG
CAAGTCGAACGAGATCCTTCGGGGTCTAGTGGCGCACGGGTGCGTAACGC
GTGGGAATCTGCCTTGGGGTTCGGAATAACTCCCCGAAAGGGGTGCTAAT
ACCGGATGATGTCGAAAGACCAAAGATTTATCGCCCTGAGATGAGCCCGC
GTAGGATTAGCTAGTTGGTGTGGTAAAGGCGCACCAAGGCGACGATCCTT
AGCTGGTCTGAGAGGATGATCAGCCACACTGGGACTGAGACACGGCCCAG
ACTCCTACGGGAGGCAGCAGTGGGGAATATTGGACAATGGGCGAAAGCCT
GATCCAGCAATGCCGCGTGAGTGATGAAGGCCTTAGGGTTGTAAAGCTCT
TTTACCCGGGAAGATAATGACTGTACCGGGAGAATAAGCCCCGGCTAACT
CCGTGCCAGCAGCCGCGGTAATACGGAGGGGCTAGCGTTGTTCGGAATT
ACTGGGCGTAAAGCGCACGTAGGCGGCTTTGTAAGTCAGAGGTGAAAGCC
TGGAGCTCAACTCCAGAACTGCCTTTGAGACTGCATCGCTTGAATCCAGG
AGAGGTGAGTGGAATTCCGAGTGTAGAGGTGAAATTCGTAGATATTCGGA
AGAACACCAGTGGCGAAGGCGGCTCACTGGACTGGTATTGACGCTGAGGT
GCGAAAGCGTGGGGAGCAAACAGGATTAGATACCCTGGTAGTCCACGCCG
TAAACGATGATAACTAGCTGTCCGGGTGCTTGGCACTTGGGTGGCGCAGC
TAACGCATTAAGTTATCCGCCTGGGGAGTACGGCCGCAAGGTTAAAACTC
AAAGGAATTGACGGGGCCTGCACAAGCGGTGGAGCATGTGGTTTAATTC
GAAGCAACGCGCAGAACCTTACCAGCGTTTGACATGGTAGGACGACTGGC
```

-continued

AGAGATGCCTTTCTTCCCTTCGGGGACCTACACACAGGTGCTGCATGGCT

GTCGTCAGCTCGTGTCGTGAGATGTTGGGTTAAGTCCCGCAACGAGCGCA

ACCCTCGACTTTAGTTACCATCATTAAGTTGGGTACTTTAAAGTAACCGC

CGGTGATAAGCCGGAGGAAGGTGGGGATGACGTCAAGTCCTCATGGCCCT

TACGCGCTGGGCTACACACGTGCTACAATGGCAAGTACAGTGGGCAGCAA

TCCCGCGAGGGTGAGCTAATCTCCAAAACTTGTCTCAGTTCGGATTGTTC

TCTGCAACTCGAGAGCATGAAGGCGGAATCGCTAGTAATCGCGGATCAGC

ATGCCGCGGTGAATACGTTCCCAGGCCTTGTACACACCGCCCGTCACACC

ATGGGAGTTGGGTTCACCCGAAGGCGTTGCGCTAACTCGTAAGAGAGGCA

GGCGACCACGGTGGGCTTAGCGACTGGGGTGAAGTCGTAACAAGGTAGCC

GTAGGGGAACCTGCGGCTGGATCACCTCCTT.

The said ZD001 (CCTCC NO: M 209198) strain is characterized in that: Gram-negative bacillus; non-spore-forming; straight rod in shape; colonies on nutrient agar plates showing the ivory-white color; positive in oxidase test; positive in catalase test; obligate aerobe; decomposing glucose, fructose, xylose and saccharose; positive in starch hydrolysis test; incapable of liquidizing gelatin; no growth at 43° C.; the size of cells being in the range of 1.5~5.0 μm×0.8-1.0 μm; and no production of yellow pigments.

The present invention also relates to the use of the said ZD001 (CCTCC NO: M 209198) stain in the preparation of gellan gum via microorganism fermentation.

In particular, the said use is described as follows. The said ZD001 (CCTCC NO: M 209198) strain is activated by routine methods, the seed obtained thereof is cultured and the cultured seed is inoculated into the fermentation medium usually suitable for the growth of Sphingomonas strains. Then, at the temperatures ranging 28~32° C. and pH 6.8~7.2, the culture is cultured on a shaker for 32~60 hrs and thereby the high acyl gellan gum-containing fermentation broth is obtained. The fermentation broth can be directly separated and extracted to obtain the high acyl gellan gum product, or it can be subjected to a deacylation treatment to prepare the low acyl gellan gum.

When the product to be prepared is a high acyl gellan gum, the method is conducted as follows. The pH value of the said high acyl gellan gum-containing fermentation broth is adjusted to 5.0~6.0, and the temperature is raised up to 50° C.~70° C. (preferably, 60° C.), and the temperature is kept constant for 30 min~2 h (preferably, 1 h). After this, the temperature is lowered to 40° C.~50° C., the pH is adjusted to 7.0, and then, lysozyme and alkaline proteinase are added and the temperature is kept as it was for 1 h~3 h (preferably, 2 h) to remove the proteins. Into the fermentation broth that the proteins have been removed, a flocculating agent solution is added to conduct the flocculation (the amount of the flocculating agent solution is about 5% of the fermentation broth in volume after the proteins have been removed). After a second separation (via the addition of isopropanol or ethanol solution having a concentration of more than 90% in the amount of about 30% of the volume of the fermentation broth, with the preferable of 95% isopropanol, an agitation, and a filter press by a plate-and-frame filter press device), the solid material is dried (at 90° C.) to obtain the said high acyl gellan gum. The flocculating agent is one or a mixture of more than one, of the following substances (the concentration usually is 20%, w/v): CaCl2, MgCl2, NaCl, and KCl.

When the product to be prepared is a low acyl gellan gum, the method is conducted as follows. Into the said high acyl gellan gum-containing fermentation broth, a solution of an alkali metal chloride or an alkali earth metal chloride (usually having a concentration of 20%, w/v) is added and the pH is adjusted to 11.0, then a solid-liquid separation (a solid-liquid separation via a plate-and-frame device) is conducted so that a fiber-like material 1 is obtained. The so-obtained fiber-like material 1 is mixed with water in the ratio of 1:4~6 in volume, the pH is adjusted to 2.5~4.0 (preferably, pH 3.0), a washing is conducted for 15 min~1 h (preferably, 30 min), and a filter press is given so that a fiber-liked material 2 is obtained. The so-obtained fiber-like material 2 is mixed evenly with water in the ratio of 1:9~12 in volume, and the temperature is raised up to 80° C.~90° C. (preferably, 83° C.~87° C.), and a basic agent is added to adjust the pH to 9.5~10.5 (preferably, pH 9.8~10.2). The reaction is conducted for 8 min~15 min (preferably, 10 min~12 min). After the reaction is over, the pH of the reaction liquid is adjusted to the neutral condition and a filtration aid is added (the amount of addition is 1~3%, w/v, preferably 2%) and a filtration is conducted. Into the filtrate, a flocculating agent is added (preferably, 10% in mass concentration, and the volume added is 5% of the filtrate volume) to conduct a flocculation. Then, a separation is given and the solid material obtained is dried to prepare the said low acyl gellan gum. The said alkali metal chloride or alkali earth metal chloride is one selected from the following list or a mixture of more than two substances selected from the following list: CaCl2, MgCl2, NaCl, and KCl (preferably, CaCl2). The said basic agent is one selected from the list or a mixture of more than two substances selected from the list: NaOH, KOH, and Na3PO4. The filtration aid is diatomite, perlite or a mixture thereof. The flocculating agent is one selected from the list or a mixture of two or more selected from the list: CaCl2, MgCl2, NaCl, and KCl (preferably, KCl).

The main beneficial effects of the present invention are that: a yellow pigments generation deficient Sphingomonas strain ZD001 (CCTCC NO: M 209198) is provided, whose fermentation broth does not contain yellow pigment(s) and has the color of milky white; during the extraction, the amount of ethanol or isopropanol for use is reduced; and the processing steps are simplified. All these beneficial effects improve the yield, and lower the production costs. It is helpful in the industrial production of high-quality gellan gum.

SPECIFIC EMBODIMENTS

The following parts are a further description of the present invention, with reference to the specific examples. However, the protection scope of the present invention should not be limited to the examples.

EXAMPLE 1

Isolation and Identification of ZD001 (CCTCC NO: M 209198) Stain

1. Collect earth samples under aseptic condition, dilute the samples and spread the suspensions onto YM agar medium plates;
2. Place the plates at 30° C. to culture for 5 days;
3. Pick up bacterial colonies with different colonial morphologies, and streak the individual colony on the same culture medium plates to isolate, i.e., placing at 30° C. to culture for 5 days.

The composition of YM agar medium, based on the final concentrations, are 0.30% of yeast extract, 0.30% of malt extract, 0.50% of peptone, 1.00% of glucose, 1.50% of agar, and the solvent distilled water.

Note: in the present invention, all of the concentrations in the medium refer to the mass-to-volume percent concentrations. For a component, the concentration 1% means that there is 1 g of the substance existing in the 100 ml medium.

After screenings, a yellow pigments generation deficient strain, i.e., ZD001 (CCTCC NO: M 209198) strain, is obtained. This strain is a Gram-negative bacillus; does not produce spores; and has the cells in the shape of straight rod. The colony on nutrient agar medium plate has the color of ivory white. The strain is positive in oxidase test, positive in catalase test, and is an obligate aerobe. The stain can decompose glucose, fructose, xylose and saccharose. The strain is positive in starch hydrolysis test, and does not liquidize the gelatin. The stain cannot grow at 43° C. The dimension of the bacterial bodies is 1.5-5.0 μm×0.8-1.0 μm. The stain does not produce yellow pigment(s).

EXAMPLE 2

Fermentation Process of ZD001 (CCTCC NO: M 209198)

1. Inoculate the pure stain culture into an YPG medium slant, and culture at 30° C. for 72 h;

2. Cultivation of first class seed: inoculate the slant seed into 50 mL medium for first class seed (held in a 250 mL flask) and culture at 30° C. with 200 rpm shaking for 24 h, and thereby the first class seed solution is obtained;

3. Cultivation of second class seed: inoculate the first class seed solution into 100 mL medium for the cultivation of second class seed (held in a 500 mL flask) in the amount 5% in volume ratio, and culture at 30° C. with 200 rpm shaking for 12 h, and thereby a second class seed solution is obtained;

4. Fermentation in fermentor: inoculate the second class seed solution into the fermentation medium at the amount of 5% v/v, and culture it under the conditions of 30° C., pH 6.8~7.2, ventilation of 1.0 vvm, and rotation speed of 300 rpm, for 48 hours;

5. Collection of the product from the fermentation: collect the gellan gum-containing fermentation gum produced in Step 4 after a cultivation of 48 hours.

The components and the final concentrations of YPG slant medium are: glucose 2.00%, peptone 0.50%, yeast extract 0.30%, agar 1.50%, and the solvent being distilled water, pH 7.2;

The final concentrations for the first class culture medium are: yeast extract 0.20%; beef extract 0.30%; peptone 0.50%; potassium chloride 0.10%, and the solvent being distilled water, pH 7.2;

The second class seed medium: glucose 1.50%; yeast extract 0.50%; peptone 0.50%; potassium dihydrogen phosphate 0.06%; dipotassium hydrogen phosphate 0.06%; magnesium sulfate 0.06%, and the solvent being distilled water, pH 7.2;

The fermentation medium: glucose 3.00%; yeast extract 0.05%; peptone 0.30%; potassium dihydrogen phosphate 0.06%; dipotassium hydrogen phosphate 0.10%; magnesium sulfate 0.06%; and the solvent being distilled water, pH 7.2.

EXAMPLE 3

The Preparation Process for Preparing High Acyl Gellan Gum

1. Pre-treatment of fermentation broth: take 100 L of fermentation broth, and adjust its pH with 10% (v/v) HCl to 6.0, and the temperature is raised up to 60° C. and kept the temperature constant for 1 h;

2. Removal of proteins impurities: the temperature is reduced to 40° C. and the pH is adjusted with 10% (w/v) NaOH to 7.0; and then 50 g of lysozyme (200,000 U/g, Pangbo Biological Engineering Co., Ltd) and 100 g of alkaline proteinase (20,000 U/g, Pangbo Biological Engineering Co., Ltd) and the temperature is kept constant for 2 h;

3. Precipitation via flocculation and separation: into the fermentation broth that has been subjected to the pre-treatment and the protein impurities removal, 5 L of 20% (w/v) CaCl2 solution is added and an agitation is conducted for 30 min. After this, 30 L of isopropanol is added and an additional agitation is conducted for 1 h. Then, a plate-and-frame filter press is given;

4. Drying and milling: dry the fiber-like material obtained from filter pressing at 90° C. for 2 h and mill the dried material so that a high acyl gellan gum product is obtained. It is in the form of a powder having the ivory white color, and containing 0.05~0.30% nitrogen.

EXAMPLE 4

The Preparation Process for Preparing Deacylated Gellan Gum

1. Pre-treatment of fermentation broth: take 100 L of mature fermentation broth, and add 3 L of 20% (w/v) CaCl2 solution into it, and an agitation is conducted for 10 min. After this, the pH is adjusted with 10% NaOH to 11.0, and an agitation is conducted for 3 min. Then, a plate-and-frame filter pressing is conducted and a fiber-like material is obtained thereby;

2. Washing: mix the fiber-like material pre-treated in Step 1 with water in the volume ratio of 1:5, adjust the pH with 10% HCl to 3.0, and conduct an agitation for 30 min. After this, a plate-and-frame is conducted so that a fiber-like material is obtained.

3. Deacylation treatment: mix the fiber-like material washed in Step 2 with water in the volume ratio of 1:10. The mixture is agitated evenly and the temperature is raised up to about 90° C. so that the fiber-like material is completely dissolved. The temperature is kept constant at 85° C. and 10% NaOH aqueous solution is added, and the pH value is adjusted to 9.5~10.5. The reaction is conducted for 10 min. After this, the pH is adjusted with 10% HCl to 6.0;

4. Add diatomite calculated in mass, in the amount of 2% of the volume of the material solution as obtained in above step, and keep the temperature at a temperature higher than 80° C. A filtration by a plate-and-frame filtration is conducted. After the filtration, 5% KCl solution (the mass concentration is 10%) is added into the material solution (filtrate) calculated in volume and then a plate-and-frame pressing is given;

5. Drying and milling: the gellan gum fiber-like material obtained from pressing is dried at 90° C. for 2 h. Then it is milled. And, the final product of low acyl gellan gum is obtained. The so-formed low acyl gellan gum is a milk-white powder, with the gel strength of ≥800 g/cm2 and the transmittancy of ≥80%.

What we claim is:

1. An isolated *Sphingomonas* strain (*Sphingomonas* sp.) ZD001 deficient in yellow pigment generation deposited at the China Center for Type Culture Collection (CCTCC) on Sep. 10, 2009 under accession number CCTCC No. M 209198.

2. The *Sphingomonas* strain according to claim 1, wherein the 16S rDNA of the said *Sphingomonas* strain comprises SEQ ID NO: 1.

3. The *Sphingomonas* strain according to claim 1, wherein the said *Sphingomonas* strain is Gram-negative; is non-spore-forming; is straight rod in shape; forms ivory-white colonies on nutrient agar plates; is positive in oxidase test; is positive in catalase test; is an obligate aerobe; is capable of decomposing glucose, fructose, xylose and saccharose; is positive in starch hydrolysis test; is incapable of liquidizing gelatin; does not grow at 43'C; has a cell size in the range of 1.5-5.0 μm×0.8-1.0 μm and produces no yellow pigment.

4. A method of preparing gellan gum comprising fermenting the *Sphingomonas* strain according to claim 1 to obtain gellan gum.

5. The method according to claim 4, wherein fermenting the said *Sphingomonas* strain comprises the steps of:
　　1) activating and cultivating the said *Sphingomonas* strain into a seed culture,
　　2) inoculating the seed culture into a fermentation medium suitable for the said *Sphingomonas* strain, and 3) culturing the inoculated fermentation medium at 28-32° C., pH 6.8-7.2, on a shaker for 32-60 hours to obtain an ivory-white fermentation broth containing high acyl gellan gum.

6. The method according to claim 5 further comprising obtaining high acyl gellan gum by separating and purifying high acyl gellan gum from the ivory-white fermentation broth, wherein the separating and purifying comprises the steps of:
   1) adjusting the pH value of the ivory-white fermentation broth to 5.0-6.0, and incubating the ivory-white fermentation broth at a temperature of 50-70° C. for 30 minutes to 2 hours,
   2) reducing the temperature to 40-50° C., and adjust the pH value of the ivory-white fermentation broth to 7.0,
   3) adding lysozyme and alkaline proteinase to the ivory-white fermentation broth, and maintaining the temperature for 1-3 hours to remove proteins, and
   4) adding a flocculating agent solution to the ivory-white fermentation broth to precipitate high acyl gellan gum, wherein the flocculating agent is $CaCl_2$, $MgCl_2$, NaCl, KCl, or any combination thereof.

7. The method according to claim 5, further comprising treating the ivory-white fermentation broth containing high acyl gellan gum to deacylate high acyl gellan gum, separating, and purifying to obtain low acyl gellan gum, wherein the treating, separating, and purifying comprise the steps of:
   1) adding a metal chloride solution to the ivory-white fermentation broth and adjusting the pH of the ivory-white fermentation broth to 11.0, wherein the said metal chloride is $CaCl_2$, $MgCl_2$, NaCl, KCl, or any combination thereof,
   2) conducting a solid-liquid separation to obtain a first material, which is a solid,
   3) mixing the first material with water at a volume ratio of 1:4-6, and adjusting the pH of the mixture to 2.5-4.0,
   4) washing the first material for 15 minutes to 1 hour, and pressing the washed first material to form a second material,
   5) mixing the second material evenly with water at a volume ratio of 1:9-12, adding a basic agent to adjust the pH of the mixture to 9.5-10.5, incubating the mixture at 80-90° C. for 8-15 minutes, wherein the said basic agent is NaOH, KOH, $Na_3PO_4$, or any combination thereof,
   6) adjusting the pH of the mixture to neutral, adding a filtration aid, and conduct a filtration to obtain a filtrate, wherein the said filtration aid is diatomite, perlite, or a mixture thereof, and
   7) adding a flocculating agent to the filtrate to precipitate low acyl gellan gum, and drying the precipitated low acyl gellan gum, wherein the said flocculating agent is $CaCl_2$, $MgCl_2$, NaCl, KCl, or any combination thereof.

* * * * *

SEQUENCE LISTING

<160> NUMBER OF SEQ ID NOS: 1

<210> SEQ ID NO 1
<211> LENGTH: 1481
<212> TYPE: DNA
<213> ORGANISM: Sphingomonas sp.

<400> SEQUENCE: 1

```
agagtttgat cctggctcag aacgaacgct ggcggcatgc ctaacacatg caagtcgaac      60
gagatccttc ggggtctagt ggcgcacggg tgcgtaacgc gtgggaatct gccttggggt     120
tcggaataac tccccgaaag gggtgctaat accggatgat gtcgaaagac caaagattta     180
tcgccctgag atgagcccgc gtaggattag ctagttggtg tggtaaaggc gcaccaaggc     240
gacgatcctt agctggtctg agaggatgat cagccacact gggactgaga cacggcccag     300
actcctacgg gaggcagcag tggggaatat tggacaatgg gcgaaagcct gatccagcaa     360
tgccgcgtga gtgatgaagg ccttagggtt gtaaagctct tttacccggg aagataatga     420
ctgtaccggg agaataagcc ccggctaact ccgtgccagc agccgcggta atacggaggg     480
ggctagcgtt gttcggaatt actgggcgta aagcgcacgt aggcggcttt gtaagtcaga     540
ggtgaaagcc tggagctcaa ctccagaact gcctttgaga ctgcatcgct tgaatccagg     600
agaggtgagt ggaattccga gtgtagaggt gaaattcgta gatattcgga agaacaccag     660
tggcgaaggc ggctcactgg actggtattg acgctgaggt gcgaaagcgt ggggagcaaa     720
caggattaga taccctggta gtccacgccg taaacgatga taactagctg tccgggtgct     780
tggcacttgg gtggcgcagc taacgcatta agttatccgc ctggggagta cggccgcaag     840
gttaaaactc aaaggaattg acgggggcct gcacaagcgg tggagcatgt ggtttaattc     900
gaagcaacgc gcagaacctt accagcgttt gacatggtag gacgactggc agagatgcct     960
ttcttccctt cggggaccta cacacaggtg ctgcatggct gtcgtcagct cgtgtcgtga    1020
gatgttgggt taagtcccgc aacgagcgca accctcgact ttagttacca tcattaagtt    1080
gggtacttta aagtaaccgc cggtgataag ccggaggaag gtgggggatga cgtcaagtcc    1140
tcatggccct tacgcgctgg gctacacacg tgctacaatg gcaagtacag tgggcagcaa    1200
tcccgcgagg gtgagctaat ctccaaaact tgtctcagtt cggattgttc tctgcaactc    1260
gagagcatga aggcggaatc gctagtaatc gcggatcagc atgccgcggt gaatacgttc    1320
ccaggccttg tacacaccgc ccgtcacacc atgggagttg ggttcacccg aaggcgttgc    1380
gctaactcgt aagagaggca ggcgaccacg gtgggcttag cgactggggt gaagtcgtaa    1440
caaggtagcc gtagggaac ctgcggctgg atcacctcct t                         1481
```